(12) United States Patent
Schmidt et al.

(10) Patent No.: US 9,250,179 B2
(45) Date of Patent: Feb. 2, 2016

(54) GONIOPHOTOMETRIC MEASUREMENT METHOD FOR THE CHARACTERIZATION OF PIGMENTS AND FILLERS

(75) Inventors: Christoph Schmidt, Kriftel (DE);
Christoph Hoffmann, Undenheim (DE);
Sabine Schoen, Herten (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/820,548

(22) PCT Filed: Aug. 16, 2011

(86) PCT No.: PCT/EP2011/004103
§ 371 (c)(1),
(2), (4) Date: Mar. 4, 2013

(87) PCT Pub. No.: WO2012/031664
PCT Pub. Date: Mar. 15, 2012

(65) Prior Publication Data
US 2013/0162992 A1    Jun. 27, 2013

(30) Foreign Application Priority Data

Sep. 10, 2010   (DE) .......................... 10 2010 044 956

(51) Int. Cl.
| | |
|---|---|
| *G01N 21/00* | (2006.01) |
| *G01N 21/47* | (2006.01) |
| *G01N 21/57* | (2006.01) |

(52) U.S. Cl.
CPC .............. *G01N 21/47* (2013.01); *G01N 21/57* (2013.01); *G01N 2021/575* (2013.01)

(58) Field of Classification Search
CPC .......... G01N 21/57; G01N 2021/4735; G01N 2021/4783; G01N 2021/575; G01N 21/25; G01N 21/255; G01N 21/47; G01N 21/474; G01N 21/4788; G01N 2201/0221; G01N 2500/02; G01N 33/3845; G01N 33/6881
See application file for complete search history.

(56) References Cited

U.S. PATENT DOCUMENTS

| | | | | |
|---|---|---|---|---|
| 4,479,718 | A | * | 10/1984 | Alman ......................... 356/405 |
| 4,917,495 | A | * | 4/1990 | Steenhoek ................... 356/328 |
| 5,252,836 | A | | 10/1993 | Matthews et al. |
| 6,064,487 | A | | 5/2000 | Kettler et al. |

(Continued)

FOREIGN PATENT DOCUMENTS

| | | |
|---|---|---|
| DE | 197 20 887 | 11/1998 |
| DE | 20 2004 011 811 | 12/2005 |

(Continued)

OTHER PUBLICATIONS

International Search Report for PCT/EP2011/004103, Date of the actual completion of international search: Nov. 7, 2011, Date of mailing of the international search: Nov. 17, 2011.

(Continued)

*Primary Examiner* — Michael P Stafira
(74) *Attorney, Agent, or Firm* — Millen White Zelano and Branigan, PC; John Sopp; Anthony Zelano (57) ABSTRACT

The present invention relates to a method for the characterization of pigments and fillers in which the luminance of a pigmented transparent medium is determined against a dark background. This measurement method is particularly suitable for determining the optical properties of cosmetic fillers.

16 Claims, 4 Drawing Sheets

(56) References Cited

U.S. PATENT DOCUMENTS

| | | |
|---|---|---|
| 6,207,174 B1 | 3/2001 | Hineno et al. |
| 6,914,684 B1 | 7/2005 | Bolash et al. |
| 7,027,165 B2 * | 4/2006 | De Haas et al. ............... 356/600 |
| 7,158,672 B2 * | 1/2007 | Johansson et al. ............ 382/167 |
| 7,342,657 B2 * | 3/2008 | Hart et al. ..................... 356/319 |
| 8,374,831 B2 * | 2/2013 | Steenhoek ......................... 703/2 |
| 2002/0167669 A1 * | 11/2002 | Schwarz ....................... 356/446 |
| 2004/0252883 A1 * | 12/2004 | Johansson et al. ............ 382/162 |
| 2006/0033922 A1 | 2/2006 | Sperling et al. |
| 2007/0100026 A1 * | 5/2007 | Munro et al. ................. 523/200 |
| 2008/0081864 A1 | 4/2008 | Takano |
| 2008/0102046 A1 * | 5/2008 | Thevenet et al. ................ 424/61 |
| 2008/0210133 A1 | 9/2008 | Roesler et al. |
| 2008/0278723 A1 | 11/2008 | Merchak |
| 2010/0094601 A1 | 4/2010 | Steenhoek et al. |
| 2013/0118380 A1 | 5/2013 | Roesler et al. |

FOREIGN PATENT DOCUMENTS

| | | |
|---|---|---|
| DE | 10 2008 059 768 | 6/2010 |
| JP | H11236315 A | 8/1999 |
| JP | 2002249414 A | 9/2001 |
| JP | 2005024455 A | 1/2005 |
| JP | 2006169393 A | 6/2006 |
| JP | 2009503205 A | 1/2009 |
| JP | 2010065169 A | 3/2010 |
| WO | WO-2008 063606 | 5/2008 |

OTHER PUBLICATIONS

Maitra, P. et al., "Optical tools to assess naturalness of cosmetic films," Color Research & Application, Apr. 1, 2009, vol. 34, No. 2, pp. 170-172.

Raven, P. N. et al., "Bidirectional reflectance from pigmented coatings," Proceedings of the SPIE, The International Society for Optical Engineering SPIE, Jul. 21, 1999, vol. 3784, pp. 262-273.

English Translation of Espacenet Abstract of DE-10 2008 059 768, Publication Date: Jun. 2, 2010.

English Abstract of JP 2002249414, Publication Date: Sep. 14, 2001.

English Abstract of JP 2005024455, Publication Date: Jan. 27, 2005.

English Abstract of JP 2010065169, Publication Date: Mar. 25, 2010.

Japanese Office Action relating to Japanese Patent Application No. 2013-527480, Date of Dispatch: Apr. 14, 2015.

* cited by examiner

GONIOPHOTOMETRIC MEASUREMENT METHOD FOR THE CHARACTERIZATION OF PIGMENTS AND FILLERS

The present invention relates to a method for the characterisation of pigments and fillers in which the luminance of a pigmented surface is determined against a dark background. This measurement method is particularly suitable for determining the optical properties of cosmetic fillers.

Cosmetic fillers are widely used in virtually all cosmetic products. They essentially contribute to the sensory, mechanical and optical properties of the formulations, such as, for example, mascaras, lipsticks, lotions, creams, shower gels, hair gels, eyeliners, make-ups, soaps, loose and compact powders, powder-to-creams and nail varnishes, to mention but a few of the most important types of product.

In contrast to coloured pigments or perfumes, cosmetic fillers generally do not obviously contribute to apparent properties of cosmetics, such as colour and odour. Instead, they in many cases serve for adjustment of important applicational properties, such as, for example, viscosity of liquids, creams and lipsticks, firmness of compact powders, abrasion behaviour of powders and make-ups, skin feel and transparency or hiding power. These product properties are of crucial importance for the haptic properties of the finished product and are thus of major importance for acceptance of a product by the customer.

The characteristic properties, such as colour and odour, should if possible not be adversely affected by the principal constituents of the product, such as, for example, fillers, and the product media, such as water or oil. Cosmetic fillers are therefore generally odorless white powders having a good skin feel and good distribution behaviour in typical cosmetic media, such as, for example, water, oil, waxes, gels or nail varnishes.

On the other hand, cosmetic fillers are important raw materials for adjusting the above-mentioned product properties, such as viscosity, transparency, etc., in a targeted manner in the desired form. An abundance of different fillers which are similar in their external properties, especially colour and skin feel, but are very different in their influence on the applicational properties, is therefore offered for use in cosmetics. Consequently, specific properties which are of crucial importance for individual product development can often only be developed by time-consuming and expensive screening trials with a multiplicity of different fillers in the formulation in question.

This applies, in particular, to the influence of fillers on the optical properties of the cosmetic formulation, such as, for example, transparency or hiding power, as well as whiteness and lustre. Besides the high preparative effort of screening with finished formulations, subsequent objective assessment of finished products is difficult since there are virtually no reliable physical measurement methods for finished products, and assessments by test personnel are very time-consuming and their results are highly subjective.

There is therefore a high demand for an objective, easy-to-carry-out measurement method for the essential optical properties of fillers, in particular cosmetic fillers, in order to make an effective choice of fillers which are suitable for a specific finished-product development with little effort. In this way, the development effort in the choice of fillers can be significantly reduced.

In this application, filler is taken to mean a pulverulent additive which specifically influences, in particular, the applicational properties of cosmetic products without significantly affecting the properties which are dominant in customer perception, such as colour and odour.

Some specific fillers contribute significantly to the optical properties of, for example, creams and make-ups on the skin through their more or less strong light scattering and the more or less pronounced ability to reduce lustre ("mattifying effect").

Light scattering or also diffuse reflection means that the incident light is reflected in virtually all directions by the filler particles. Excessive scattering causes a whitish, often mask-like, unnatural appearance due to high hiding power, while low scattering causes high transparency of the applied cosmetic formulation.

Besides the hiding power and transparency of a filler, its mattifying effect is an important optical property. This refers to the ability of a cosmetic raw material to reduce or completely prevent undesired lustre on the skin. This is achieved partly by the above-described scattering by the filler particles. An essential additional effect is offered by fillers which provide the surface of the applied product film with a microstructure, which causes additional light scattering without increasing the hiding power.

This results in a particularly natural appearance of the skin. The ability of a filler to impart a particularly attractive and natural appearance on the skin due to the above-mentioned optical properties is often referred to as the soft-focus effect. To date, however, it was not possible to measure the soft-focus effect of a filler in a satisfactory manner.

Surprisingly, a measurement method has now been found which enables the optical properties of fillers to be determined in a simple manner. A reproducible measurement method has been developed by means of which the above-described optical properties of fillers, in particular of cosmetic fillers, can be measured objectively. It is a standardisable process which gives meaningful data for making a pre-selection of the fillers, from a large number of commercial fillers, whose optical properties are particularly suitable for a specific product development with respect to scattering capacity and mattifying effect.

This pre-selection enables developers of cosmetic formulations to avoid the majority of labour-intensive and expensive experimental screenings and thus to make product development more effective.

Figure 1:
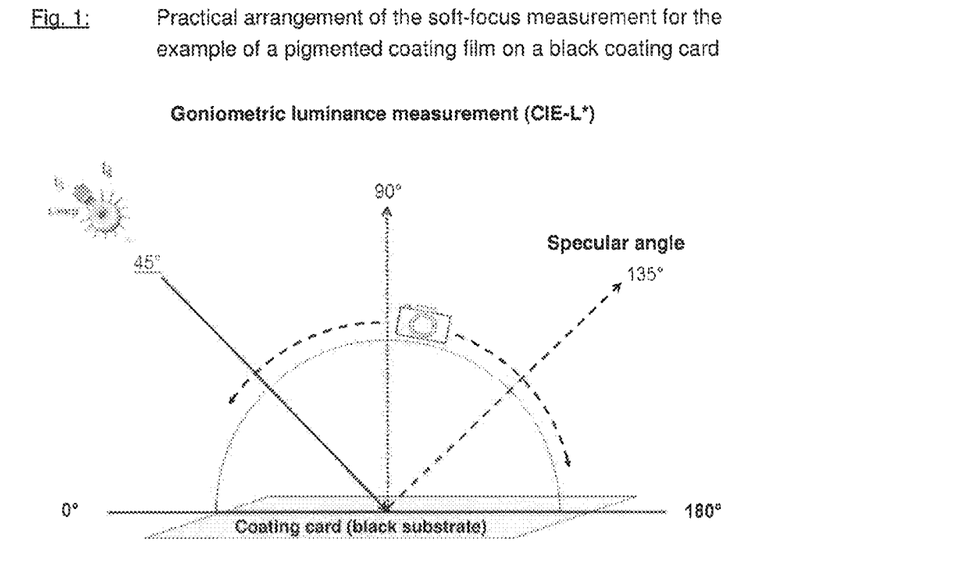
Fig. 1: Practical arrangement of the soft-focus measurement for the example of a pigmented coating film on a black coating card

The present invention thus relates to a goniochromatic measurement method for the determination of the luminance of particles having a particle size of 0.1-500 µm, characterised in that the particles are incorporated into a transparent medium and applied to a dark support or the particles are applied in powder form to a dark support, and the particles are illuminated from a fixed angle relative to the plane of the support, and the back-scattered light is measured at various angles along the semicircle above the support (FIG. 1).

The measurement method according to the invention is preferably based on the measurement of the luminance of a filler-containing coating film on a dark support, such as, for example, a black coating card. The coating card here is illuminated from a fixed angle relative to the plane of the card. The luminance is measured at various angles above the card.

In this application, a dark support is taken to mean a support which is coloured dark, for example black or dark-grey, or is coated with a dark, for example black, coating.

Besides the measurement of a pigment- or filler-containing film, it is also possible to measure a dry powder layer on a dark background. To this end, the area to be measured is covered uniformly with a thin powder layer, for example by dusting. This can preferably be carried out by firstly providing the area with a means of adhesion, for example a self-adhesive film, a double-sided adhesive tape, a rubber coating, an adhesive or a transparent lacquer, and subsequently coating it with the pigment or filler powder. The excess powder is then removed, if necessary, from the self-adhesive surface, for example by gentle tapping or a stream of air. This surface coated with dry powder in this way is then measured analogously, as described for the variant of the coating film.

The measurement is preferably carried out in the plane of the incident light at the following angles along the semicircle above the card, with an illumination angle of 45°, as depicted in FIG. 1:

| 5° |
|---|
| 15° |
| 25° |
| 65° |
| 75° |
| 85° |
| 90° |
| 95° |
| 105° |
| 115° |
| 125° |
| 135° |
| 145° |
| 155° |
| 165° |
| 175° |

Depending on the type of instrument selected, the angles 35°, 45° and 55° and further or other angles can also be measured.

The transparent medium is preferably a coating or a plastic, in particular a coating. The coating is preferably applied to a black coating card, which serves as support. If the medium is a plastic, the plastic is preferably in the form of flakes.

The support can be coated by knife coating, spraying, brushing, powder coating, printing, adhesive bonding or the like.

The concentration of the coating can be varied in broad limits in order to obtain a meaningfulness of the measurement results which is as helpful as possible for the particular application.

The support is preferably coated using a knife coater. The gap width of the knife coater can be varied in broad limits depending on the viscosity of the coating and the desired layer thickness.

In the case of the use of cosmetic fillers in a transparent medium, for example in a nitrocellulose lacquer or nail varnish, applied to a black coating card, the following conditions have proven particularly advantageous:

viscosity of the coating, for example a nitrocellulose lacquer:
  0.5-5 Pa·s, preferably 1-3 Pa·s, in particular 1.9-2.1 Pa·s
solids concentration in the wet coating material:
  0.5-10% by weight, preferably 1-5% by weight and in particular 2.5%
knife coater gap:
  50-1000 µm, preferably 500 µm.

After application of the coating by knife coating, the coating cards are preferably dried on a hotplate at preferably 40° C. for about 60 min. However, the drying process is dependent on the coating used.

In general, freely selected conditions can be used with respect to the coating selected, the filler concentration, the application method and the drying or curing of the coating, etc., but all particles to be investigated, such as, for example, fillers or pigments, must be applied and measured in the same way in order to guarantee comparability of the measurements.

The same applies to the application of the powder without a medium, i.e. in dry form, to a surface, which is optionally self-adhesive.

When selecting the measuring instrument, it must be ensured that a goniometer having a sufficiently large measurement angle range is selected, so that measurements can be carried out at least from 90° (perpendicularly above the coating card) to the specular angle (for example 135° in the case of an illumination angle of 45°).

It is important in the measurement method according to the invention that the luminance is indicated in one of the standard colour systems CIEL*a*b*, CIELUV, CIEXYZ, CIEYUV or YUV, i.e. the value L*, L, X or Y is determined for the luminance, depending on the standard colour system.

The present invention is carried out using the "Lambda 900" spectrometer (manufacturer: Perkin Elmer) with "ARTA" (automated reflectance/transmittance analyser) goniometer attachment, which records the entire semicircle (180°) above the coating card. Under certain circumstances, it may not be possible to measure all angles in the range of the illumination incidence angle for constructional reasons, but this has only little effect on the meaningfulness of the measurement.

The luminance profile obtained using the measurement method described here shows the crucial properties of the fillers for the soft-focus effect in a transparent medium, for example a coating film, which is basically comparable with a cream, lotion, make-up or the like applied to the skin.

The measurement results and the determination of key performance indicators (KPIs) of various cosmetic fillers are described below and the use and benefits of the measurement method according to the invention are thus explained.

The method can basically be used for particles, in particular finely divided fillers and pigments. The measurement method according to the invention is suitable for particle sizes of 0.1-500 µm, preferably 1-250 µm, in particular 1-50 µm and very particularly preferably 0.5-30 µm. Suitable particles are, in particular, selected from the group of synthetic organic polymers, polymethyl methacrylate, methyl methacrylate cross-polymer, natural mica, synthetic mica, (natural or synthetic) mica flakes coated with one or more metal oxides, coated or uncoated $SiO_2$ flakes, coated or uncoated $Al_2O_3$ flakes, nylon powder, pure or filled melamine resins, talc, $SiO_2$, glass powder, glass beads, coated or uncoated glass flakes, BiOCl, oxides or hydroxides of aluminium, magnesium, calcium or zinc, barium sulfate, calcium sulfate, calcium carbonate, magnesium carbonate, basic alkaline-earth metal carbonates, carbon, boron nitride, zeolites, bentonites, alkali metal aluminium silicate beads coated with titanium dioxide and silicon dioxide, silicates of aluminium, magnesium, calcium, barium or zinc, or alkali metal silicates of aluminium, magnesium, calcium, barium or zinc.

The coated mica flakes, $SiO_2$ flakes, $Al_2O_3$ flakes or glass flakes are preferably coatings with one or more metal oxides. The metal oxides are preferably selected from the group $TiO_2$, $Fe_2O_3$, $Fe_3O_4$, $Al_2O_3$ and $SiO_2$.

The following application to cosmetic fillers should be regarded as illustrative and is in no way intended to restrict the invention.

Figure 2:
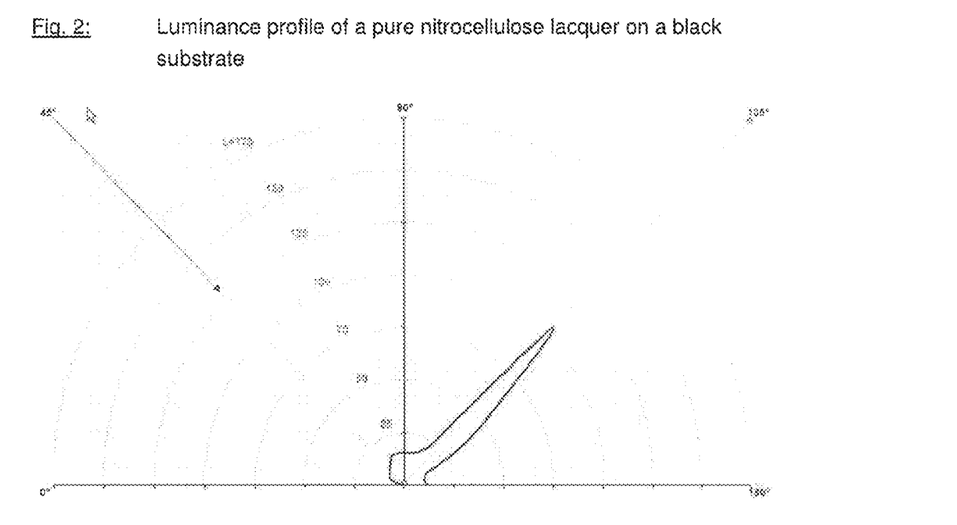
Fig. 2: Luminance profile of a pure nitrocellulose lacquer on a black substrate

FIG. 2 shows the luminance profile of pure nitrocellulose lacquer in the CIE L*a*b* colour system, measured using the "Lambda 900" spectrometer (manufacturer: Perkin Elmer) with "ARTA" (automated reflectance/transmittance analyser) goniometer attachment. With L*=about 110, it exhibits very high luminance at the specular angle (45°/135°), while the luminance drops rapidly to very low L values of about 10-15 outside the specular angle. The high luminance at the reflection angle can be explained by the smooth surface of the unpigmented coating and its strong mirror action. Outside the specular angle, the L* values are low, since the coating has no scattering action for light owing to its high transparency, and at the same time the light passing through the coating is completely absorbed by the black substrate.

Figure 3:
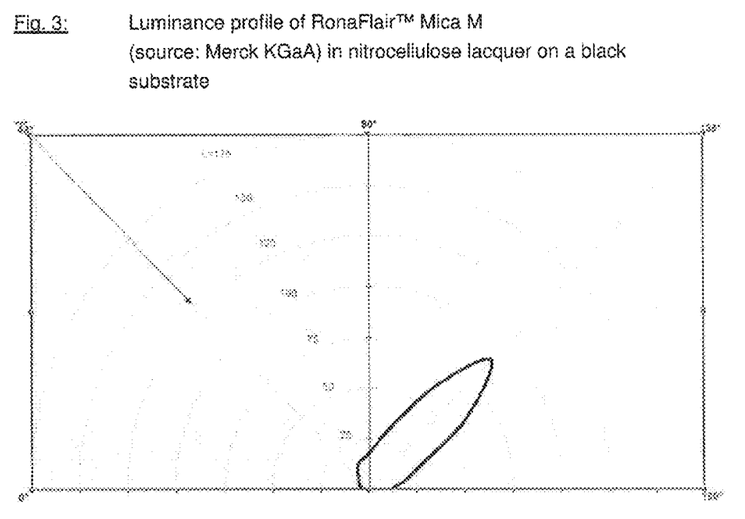
Fig. 3: Luminance profile of RonaFlair™ Mica M
(source: Merck KGaA) in nitrocellulose lacquer on a black substrate

FIG. 3 shows the luminance profile of the filler RonaFlair™ Mica M (product from Merck KGaA).

RonaFlair™ Mica M consists of thin, finely divided mica flakes having a particle size of 0.5-15 μm, which are embedded parallel to the coating plane and therefore only adversely affect the surface of the coating to an insignificant extent. The surface lustre of the coating layer is therefore still very strong. The mica flakes have a low refractive index, i.e. n≤1.8 (mica: n=1.5), and therefore only scatter the light very little. The luminance curve is therefore only slightly broadened compared with the pure coating. In agreement with this result, RonaFlair™ Mica M is a filler having only a slight influence on the optical properties of a formulation and with no pronounced soft-focus effect.

Figure 4:
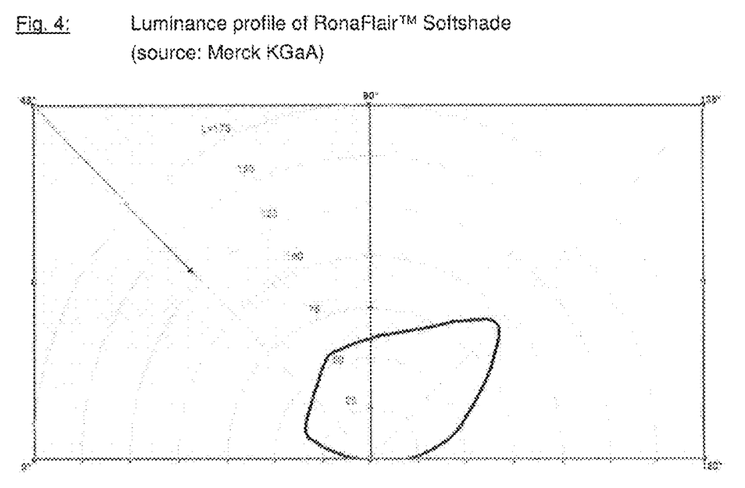
Fig. 4: Luminance profile of RonaFlair™ Softshade
(source: Merck KGaA)

FIG. 4 shows the luminance profile of RonaFlair™ Softshade (product from Merck KGaA). This filler consists of mica flakes having a particle size of 0.5-15 μm whose scattering capacity is increased by a coating with aluminium oxide, silicon dioxide and titanium dioxide. Accordingly, it exhibits significantly greater luminance outside the specular angle than RonaFlair™ Mica M. The coating surface is also very smooth in the case of this filler, meaning that significant lustre, i.e. an increased L* value, is also measured at 45°/135° here.

The scattering behaviour of RonaFlair™ Softshade provides this filler with good properties for optical compensation of irregularities in the skin, such as, for example, pigment spots and wrinkles.

The relatively high lustre component of this filler, which is evident from the luminance curve, makes it particularly suitable for formulations which have the aim of a natural appearance of the skin in combination with moderate surface lustre.

Figure 5:
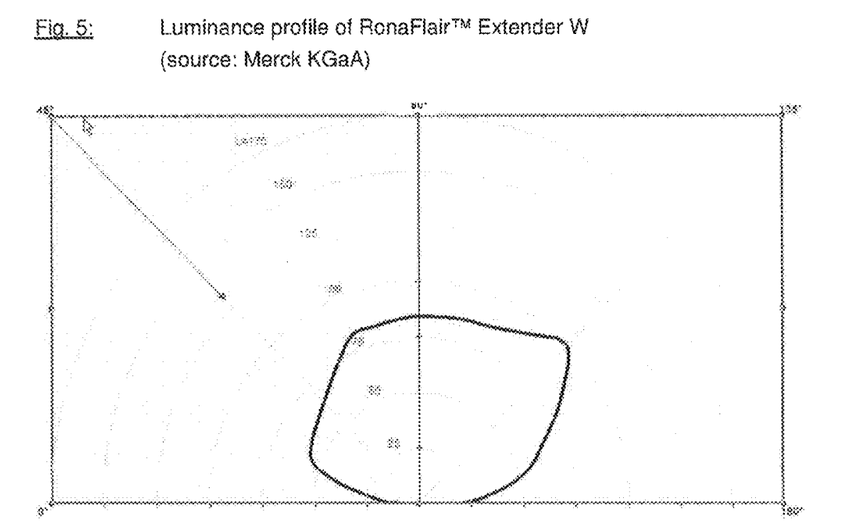
Fig. 5: Luminance profile of RonaFlair™ Extender W
(source: Merck KGaA)

FIG. 5 shows the luminance profile of RonaFlair™ Extender W (manufacturer: Merck KGaA), which has a significantly higher scattering capacity compared with RonaFlair™ Softshade. It therefore exhibits significantly higher L* values in all directions, but there is only a slight increase at the specular angle compared with the other angles. Accordingly, RonaFlair™ Extender W has a substantially circular remission curve. This means that RonaFlair™ Extender W scatters light very uniformly in all directions and in addition provides the coating surface with a microtexture, which results in a matt, velvet-like appearance.

The property of specific skin cosmetics of providing a particularly natural appearance without interfering lustre effect due to a light-scattering effect and a mattifying action on the surface is frequently referred to as the soft-focus effect. Functional fillers and pigments have crucial importance in achieving the soft-focus effect. There is hitherto no general definition and no meaningful measurement method for the soft-focus effect.

Figure 6:
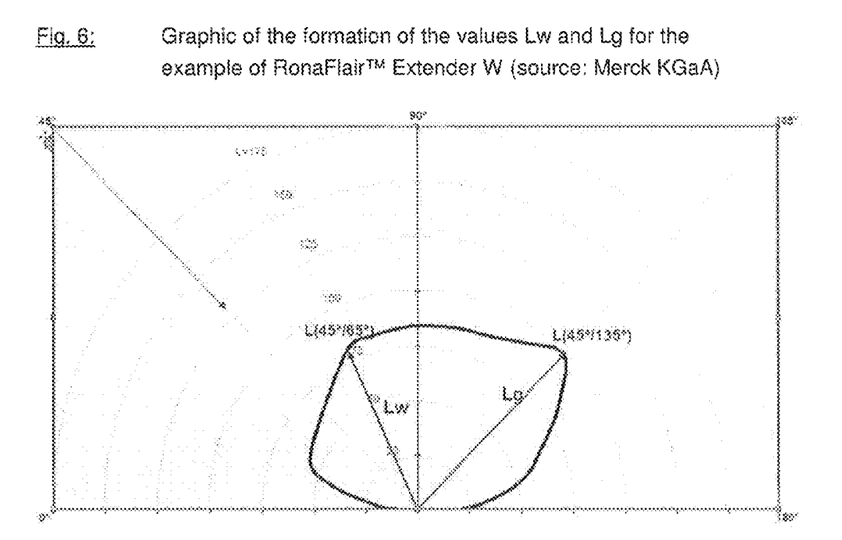
Fig. 6: Graphic of the formation of the values Lw and Lg for the
example of RonaFlair™ Extender W (source: Merck KGaA)

The present invention therefore provides a measurement method which enables simple and reproducible quantification of the two optical properties—whiteness and mattifying effect which are essential for the soft-focus effect. For rapid determination of these two properties, two key performance indicators (KPIs) are formed from the measurement data: in the embodiment described in greater detail here in the CIE L*a*b* colour system, these are the luminance value L* at 65° (=Lw) as a measure of the whiteness and the hiding power, and the quotient Lw/Lg for the uniformity of the scattered-light distribution over the various viewing angles. Lg is the L* value at the specular angle (cf. FIG. 6):

1. Lw describes the luminance or whiteness of the filler.

Highly transparent fillers have a low Lw value of <20, for example RonaFlair™ Mica M with Lw=13.8, whereas strongly hiding, white fillers have a high Lw value of >65, for example RonaFlair™ Extender W with Lw=80.5.

2. The quotient Lw/Lg=SFF (soft-focus factor) describes the lustre-reducing action of the filler (mattifying effect).

Lw/Lg can also be regarded as a measure of the circularity of the goniometric luminance curve.

According to this definition, an ideal soft-focus filler has an SFF of 1.0, whereas a neutral or lustre-supporting filler has a very low SFF of <0.3.

Figure 7:
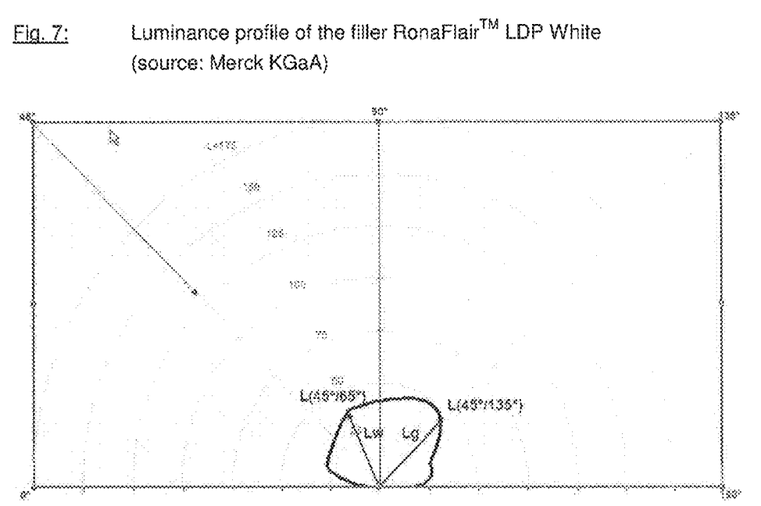
Fig. 7: Luminance profile of the filler RonaFlair™ LDP White
(source: Merck KGaA)

A particularly good soft-focus filler has low to moderate whiteness Lw and at the same time a high mattifying effect, which is described by the soft-focus factor SFF defined above. In cosmetic products, these two properties support to a large extent a uniform and natural appearance of the skin. These properties are achieved, for example, by the filler from Example 1 (RonaFlair™ LDP White), as can be seen from FIG. 7.

Preferred fillers have an Lw value of 100>x>20, in particular 60>x>25, and an Lg value of 140>x>30, in particular 85>x>35.

Fillers having good soft-focus properties have an SFF value in the range 0.5-1.0, in particular 0.7-1.0.

The following examples are intended to explain the invention, but without limiting it.

EXAMPLES

The fillers to be investigated are incorporated into a nitrocellulose lacquer.

Preparation of the Nitrocellulose Lacquer:

0.5 kg of collodium wool is dissolved in a mixture of 2.1 kg of n-butyl acetate and 1.5 kg of ethyl acetate. A solution of 0.65 kg of Acronal 700 L in 0.65 kg of ethyl acetate and 0.6 kg of toluene is subsequently stirred in. Finally, the viscosity of the lacquer is measured and if necessary adjusted to a value between 1.9 and 2.1 Pa·s by addition of a mixture of 1.4 parts of n-butyl acetate and 1 part of ethyl acetate.

Coating of Coating Cards with Nitrocellulose Lacquer;

1.25 g of filler powder are stirred uniformly into 50 g of the nitrocellulose lacquer described above, and the mixture is left to stand for 45 minutes for degassing.

The lacquer is applied to the coating card using a knife coater having a gap width of 500 μm at an application rate of about 1 m/min. After application of the lacquer by knife coating, the coating cards are dried on a hotplate at about 40° C. for 60 min.

The subsequent measurement is carried out using a "Lambda 900" spectrometer (manufacturer: Perkin Elmer) with "ARTA" (Automated Reflectance/Transmittance Analyser) goniometer attachment, which records the entire semicircle (180°) above the coating card.

Table 1 shows the key performance indicators determined of various commercially available functional fillers.

| | Lw 45°/65° (whiteness) | Lg 45°/135° (L at the specular angle) | Soft-focus factor SFF (Lw/Lg) |
|---|---|---|---|
| RonaFlair™ Mica M (mica) (source: Merck KGaA) | 13.84 | 90.47 | 0.15 |
| Talc (source: Merck KGaA) | 16.14 | 76.77 | 0.21 |
| RonaFlair™ Softshade ($SiO_2$-, $Al_2O_3$- and $TiO_2$- coated mica) (source: Merck KGaA) | 54.35 | 93.81 | 0.58 |
| RonaFlair™ Extender W ($TiO_2$-coated mica) (source: Merck KGaA) | 80.47 | 100.14 | 0.8 |
| RonaFlair™ LDP ($TiO_2$- and $Fe_2O_3$-coated $SiO_2$ beads) (source: Merck KGaA) | 45.15 | 62.63 | 0.72 |
| Experimental Example 1 RonaFlair™ LDP White (source: Merck KGaA) | 39.37 | 44.07 | 0.89 |
| TRES BN PUHP3016 (boron nitride) source: Saint-Gobain | 66.09 | 79.12 | 0.83 |
| Orgasol 2002 D NAT COS (nylon) (source: Arkema) | 31.73 | 37.93 | 0.84 |
| Coverleaf AR80 (talc coated with $SiO_2$ and $Al_2O_3$) (source: Presperse Inc.) | 43.6 | 53.17 | 0.82 |
| Silica beads SB700 ($SiO_2$ beads) (source: U.S. Cosmetics Inc.) | 23.67 | 37.25 | 0.63 |

Consideration of these key performance indicators allows developers of cosmetic formulations to make an appropriate pre-selection of fillers. For example, for a product having particularly good soft-focus properties and moderate transparency, fillers having a high SFF and a moderate luminance value Lw are particularly suitable, for example the filler RonaFlair™ LDP White from Example 1. For a cosmetic formulation having a good soft-focus action and a higher luminance or higher hiding power, a filler having a high SFF and a high Lw value will be suitable, for example RonaFlair™ Extender W.

A filler selection of this type can easily be made from a large number of commercial raw materials with reference to the goniometric measurements described and the key performance indicators derived therefrom, and the effort for experimental screening of various fillers in finished products can thus be greatly reduced.

The preparation of a filler is described in a representative manner using the example of the commercially available filler RonaFlair™ LDP White (product from Merck KGaA).

Example 1

Preparation of RonaFlair™ LDP White (Titanium Dioxide- and Silicon Dioxide-Coated Alkali Metal Aluminium Silicate Beads)

250 g of spherical alkali metal aluminium silicate beads (silica-alumina-ceramic beads; Zeeospheres W-210, 1-12 µm; manufacturer 3M) are suspended in 1.8 l of deionised water and heated to 75° C. with vigorous stirring. An amount of 395 g of $TiCl_4$ solution (30%) is metered into this mixture at pH 2.2 at a rate of 3.3 ml/min, and the pH is kept constant using sodium hydroxide solution (32%). The pH is then adjusted to 8.0 using sodium hydroxide solution (32%), and 383 g of sodium water-glass solution (13% of $SiO_2$, Merck KGaA) are metered in at this pH at a rate of 1.7 ml/mm. The pH is kept constant using hydrochloric acid (18%).

For work-up, the pigment is filtered off, washed with 15 l of deionised water, dried at 110° C. for 16 hours and sieved through a sieve having a mesh width of 32 µm.

This gives a pure-white powder having a very soft skin feel which is highly suitable as filler for cosmetic formulations, for example compact powders, lipsticks and pure-white emulsions and creams.

Use Examples

Example A1

Creamy Eyeshadow

| Raw material | | INCI | [%] |
|---|---|---|---|
| Phase A | | | |
| Colorona Light Blue | (1) | MICA, CI 77891 (TITANIUM DIOXIDE) CI 77510 (FERRIC FERROCYANIDE) | 10.00 |
| TRES BN PUHP3016 | (5) | boron nitride | 15.00 |
| Talc | (1) | Talc | 12.00 |
| Phase B | | | |
| Crodamol PMP | (2) | PPG-2Myristyl Ether Propionate | 32.80 |
| Miglyol 812 N | (3) | Caprylic/Capric Triglyceride | 12.00 |
| Syncrowax HGLC | (2) | C18-36 Acid Triglyceride | 10.00 |
| Syncrowax HRC | (2) | Tribehenin | 3.00 |
| Parteck® LUB STA | (1) | Stearic Acid | 3.00 |
| Antaron V-216 | (4) | PVP/Hexadecene Copolymer | 2.00 |
| Oxynex® K liquid | (1) | PEG-8, Tocopherol, Ascorbyl Palmitate, Ascorbic Acid, Citric Acid | 0.10 |
| Propyl 4-hydroxy-benzoate | (1) | Propylparaben | 0.10 |

Preparation:

Heat phase B to about 80° C. until everything has melted and cool to 65° C. with stirring. Then add the ingredients of phase A with stirring, and pour the mass into the proposed packaging at 65° C. Allow to cool to room temperature.

The use of the fillers boron nitride and talc enables the lustre in the eyeshadow to be adjusted specifically.

Sources of Supply:
(1) Merck KGaA/Rona®
(2) Croda GmbH
(3) Sasol Germany GmbH
(4) ISP Global Technologies
(5) Saint-Gobain

Example A2

Creamy Eyeshadow

| Raw material | | INCI | [%] |
|---|---|---|---|
| Phase A | | | |
| Colorona Light Blue | (1) | MICA, CI 77891 (TITANIUM DIOXIDE) CI 77510 (FERRIC FERROCYANIDE) | 10.00 |

-continued

| Raw material | | INCI | [%] |
|---|---|---|---|
| Mica M | (1) | MICA | 15.00 |
| Talc | (1) | Talc | 12.00 |
| Phase B | | | |
| Crodamol PMP | (2) | PPG-2Myristyl Ether Propionate | 32.80 |
| Miglyol 812 N | (3) | Caprylic/Capric Triglyceride | 12.00 |
| Syncrowax HGLC | (2) | C18-36 Acid Triglyceride | 10.00 |
| Syncrowax HRC | (2) | Tribehenin | 3.00 |
| Parteck ® LUB STA | (1) | Stearic Acid | 3.00 |
| Antaron V-216 | (4) | PVP/Hexadecene Copolymer | 2.00 |
| Oxynex ® K liquid | (1) | PEG-8, Tocopherol, Ascorbyl Palmitate, Ascorbic Acid, Citric Acid | 0.10 |
| Propyl 4-hydroxy-benzoate | (1) | Propylparaben | 0.10 |

Preparation:

Heat phase B to about 80° C. until everything has melted and cool to 65° C. with stirring. Then add the ingredients of phase A with stirring, and pour the mass into the proposed packaging at 65° C. Allow to cool to room temperature.

The use of the fillers mica and talc enables the preparation of a very transparent eyeshadow which has significantly lower lustre compared with Example A1.

Sources of Supply:
(1) Merck KGaA/Rona®
(2) Croda GmbH
(3) Sasol Germany GmbH
(4) ISP Global Technologies
(5) Saint-Gobain Example A3

Face Powder

| Raw material | | INCI | [%] |
|---|---|---|---|
| Phase A | | | |
| Pigment according to Example 1 | (2) | Sodium Potassium Aluminum Silicate Titanium Dioxide Silicon Dioxide | 20.00 |
| Unipure Yellow LC 182 | (1) | CI 77492 (Iron Oxides) | 1.20 |
| Unipure Red LC 381 | (1) | CI 77491 (Iron Oxides) | 0.20 |
| Unipure Brown LC 889 | (1) | CI 77491 (Iron Oxides) CI 77499 (Iron Oxides) | 0.30 |
| Magnesium stearate | (2) | Magnesium Stearate | 2.00 |
| Talc | (2) | Talc | 71.90 |
| Phase B | | | |
| RonaCare ® all-rac-alpha-tocopheryl acetate | (2) | Tocopheryl Acetate | 0.30 |
| Perfume oil 200 529 | (3) | Parfum | 0.30 |
| Eutanol G | (4) | Octyldodecanol | 3.70 |
| Propyl 4-hydroxy-benzoate | (2) | Propylparaben | 0.10 |

Preparation:

Add the constituents of phase A to the mixer (for example La Moulinette from Moulinex) and mix for 2×10 seconds. Transfer the mixture into a beaker, add the binder dropwise, and stir in advance using the spatula. Again add the mixture with binder to the mixer and process for 3×10 seconds to give a homogeneous phase.

This gives a face powder which improves the skin feel and, due to optical compensation, enables wrinkles to substantially disappear.

Notes:

The pressing pressure for a powder compact with a diameter of 36 mm is about 25 bar.

Sources of Supply:
(1) Les Colorants Wackherr
(2) Merck KGaA/Rona®
(3) Fragrance Resources
(4) Cognis GmbH Example A4

Mattifying Foundation

| Raw material | | INCI | [%] |
|---|---|---|---|
| Phase A | | | |
| Water, demineralised | | Aqua (Water) | 57.89 |
| Pigment according to Example 1 | (1) | Sodium Potassium Aluminum Silicate Titanium Dioxide Silicon Dioxide | 6.00 |
| Glycerin (87% extra pure) | (1) | Glycerin, Aqua (Water) | 5.00 |
| RonaCare ® Ectoin | (1) | Ectoin | 0.30 |
| Keltrol CG-SFT | (2) | Xanthan Gum | 0.15 |
| Triethanolamine 90% care | (3) | Triethanolamine, Aqua (Water) | 0.13 |
| Phase B | | | |
| Kronos 1001 | (4) | CI 77891 (Titanium Dioxide) | 4.92 |
| Unipure Yellow LC 182 | (5) | CI 77492 (Iron Oxides) | 1.60 |
| Unipure Red LC 381 | (5) | CI 77491 (Iron Oxides) | 0.20 |
| Unipure Brown LC 889 | (5) | CI 77491 (Iron Oxides) CI 77499 (Iron Oxides) | 0.20 |
| Unipure Blue LC 686 | (5) | CI 77007 (Ultramarin Blue) | 0.08 |
| Phase C | | | |
| Miglyol 812N | (6) | Caprylic/Capric Triglyceride | 7.00 |
| Eutanol G | (7) | Octyldodecanol | 4.00 |
| Montanov 202 | (8) | Arachidyl Alcohol, Behenyl Alcohol, Arachidylglucoside | 4.00 |
| Avocado oil | (9) | Persea Gratissima (Avocado Oil) | 2.00 |
| Eusolex ® 9020 | (1) | Butyl Methoxydibenzoylmethane | 1.50 |
| Hydrolite-5 | (10) | Pentylene Glycol | 1.20 |
| Bentone gel GTCC V | (11) | Stearalkonium Hectorite, Propylene Carbonate, Caprylic/Capric Triglyceride | 1.00 |
| RonaCare ® all-rac-alpha-tocopheryl acetate | (2) | Tocopheryl Acetate | 0.50 |
| Phenonip | (12) | Phenoxyethanol, Butylparaben, Ethylparaben, Propylparaben, Methylparaben | 0.40 |
| Oxynex ® K liquid | (1) | PEG-8, Tocopherol, Ascorbyl Palmitate, Ascorbic Acid, Citric Acid | 0.03 |
| Phase D | | | |
| Simulgel EG | (8) | Sodium Acrylate/Sodium Acryloyldimethyltaurate Copolymer, Isohexadecane, Polysorbate 80 | 0.60 |
| Phase E | | | |
| Water, demineralised | | Aqua (Water) | 1.00 |

Preparation;

Slowly add the Keltrol to the water of phase A and disperse. Scatter in the remaining constituents of phase A with stirring.

Add the constituents of phase B to phase A and homogenise for 3 min using the Ultra-Turrax T25 (red-blue setting, 13,500-20,500 rpm) and check for agglomerates. Heat phases A/B and phase C separately to 75° C. Add phase C to phases A/B with stirring and homogenise for 2 min using the Ultra-Turrax T25 (yellow-green setting, 8000-9500 rpm). Add phase D at between 55-60° C., add phase E at 40° C., cool to room temperature with further stirring; adjust pH to 7.0 using 30% citric acid. Then transfer into suitable containers.

This gives a light, weakly hiding foundation which is suitable for all skin types, improves the skin feel and, due to optical compensation, enables wrinkles to substantially disappear.

Sources of Supply:
(1) Merck KGaA/Rona®
(2) C.P. Kelco
(3) BASF AG
(4) Kronos International Inc.
(5) Les Colorants Wackherr
(6) Sasol Germany GmbH
(7) Cognis GmbH
(8) Seppic
(9) Gustav Heess GmbH
(10) Symrise
(11) Elementis Specialities
(12) Clariant GmbH Example A5

Body Lotion

| Raw material | | INCI | [%] |
|---|---|---|---|
| Phase A | | | |
| Aloe vera gel 10x decolourised | (1) | ALOE BARBADENSIS | 2.00 |
| D-Panthenol | (2) | PANTHENOL | 0.40 |
| Pigment from Example 1 | (3) | Sodium Potassium Aluminum Silicate Titanium Dioxide Silicon Dioxide | 6.00 |
| RonaCare® allantoin | (3) | ALLANTOIN | 0.20 |
| Glycerin, anhydrous | (3) | GLYCERIN | 4.00 |
| Water, demineralised | | AQUA (WATER) | 67.57 |
| Phase B | | | |
| Protelan AGL 95/C | (4) | SODIUM COCOYL GLUTAMATE | 6.00 |
| Cosmacol EMI | (5) | DI-C12-13 ALKYL MALATE | 3.00 |
| Eutanol G | (6) | Octyldodecanol | 3.00 |
| Jojoba oil | (7) | SIMMONDSIA CHINENSIS (JOJOBA OIL) | 1.50 |
| Tegosoft TN | (8) | C12-15 Alkyl Alkyl benzoate | 1.50 |
| Carbopol ETD 2020 | (9) | Acrylates/C10-30 Alkyl Acrylate Crosspolymer | 0.60 |
| Phenonip | (10) | Phenoxyethanol, Butylparaben, Ethylparaben, Propylparaben, Methylparaben | 0.60 |
| RonaCare® bisabolol | (3) | Bisabolol | 0.50 |
| RonaCare® all-rac-alpha-tocopheryl acetate | (3) | Tocopheryl Acetate | 0.50 |
| Oxynex® ST liquid | (3) | Diethylhexyl Syringylidenemalonate, Caprylic/Capric Triglyceride | 0.50 |
| Cremophor RH 410 | (11) | PEG-40 Hydrogenated Castor Oil | 0.30 |
| Oxynex® K liquid | | PEG-8, Tocopherol, Ascorbyl Palmitate, Ascorbic Acid, Citric Acid | 0.03 |
| Phase C | | | |
| Perfume oil Lifetime DH10255/1 | (12) | Parfum | 0.50 |
| Phase D | | | |
| Water, demineralised | | Aqua (Water) | 1.00 |
| Germal 115 | (13) | Imidazolidinyl Urea | 0.30 |

Preparation:

Pre-dissolve the aloe vera and RonaCare® allantoin in the water of phase A with stirring, then add the other constituents of phase A and heat to 60° C. Place the jojoba oil, Oxynex K liquid, Cosmacol EMI, Eutanol G and Tegosoft TN in a stirred vessel, then homogeneously incorporate the Carbopol using the dispersion disc (about 700 rpm, 20 min). Then add the remaining constituents of phase B and stir everything to give a homogeneous mixture, only adding the Protelan AGL 95/C to phase B right at the end in order to avoid excessive introduction of air. Slowly emulsify phase A into phase B (RT) at 60° C. with the aid of the dispersion disc. Add phases C and D, then homogenise for 4 min using the Ultra-Turrax T50, setting 4. Cool to room temperature.

pH (23° C.)=5.5-6.0

Viscosity: Brookfield DV II+Helipath, spindle C, 5 rpm, 24° C.=11,200 mPa s

This gives a body lotion which is suitable for all skin types and improves the skin feel.

Sources of Supply:
(1) Terry Laboratoires
(2) Alfa Aesar GmbH & Co. KG
(3) Merck KGaA/Rona®
(4) Zschimmer & Schwarz GmbH & Co
(5) Nordmann, Rassmann GmbH & Co.
(6) Cognis GmbH
(7) Gustav Heess GmbH
(8) Evonik Goldschmidt GmbH
(9) Noveon
(10) Clariant GmbH
(11) BASF AG
(12) Parfex
(13) ISP Global Technologies

The invention claimed is:

1. Goniochromatic measurement method for the determination of the luminance of particles having a particle size of 0.1-500 μm, comprising: incorporating the particles into a transparent medium and applying the medium with the particles to a dark support or applying the particles in powder form to a dark support; and then illuminating the particles on the support from a fixed angle relative to the plane of the support, and measuring the back-scattered light at multiple different angles along a semicircle extending above the plane of the dark support.

2. Goniochromatic measurement method according to claim 1, wherein the luminance is indicated in one of the standard colour systems CIEL*a*b*, CIELUV, CIEXYZ, CIEYUV or YUV.

3. Goniochromatic measurement method according to claim 1, wherein the particles are incorporated into a transparent medium and the transparent medium is a plastic.

4. Goniochromatic measurement method according to claim 1, wherein the particles are incorporated into a transparent medium and the transparent medium comprises a plastic flake.

5. Goniochromatic measurement method according to claim 1, wherein the particles are incorporated into a transparent medium and the transparent medium is a coating film comprising the particles, where this coating film is applied to a black coating card as the dark support.

6. Goniochromatic measurement method according to claim 1, wherein the particles are incorporated into a transparent medium and the transparent medium comprises 1-30% by weight of the particles.

7. Goniochromatic measurement method according to claim 3, wherein the plastic transparent medium comprises 1-30% by weight of the particles.

8. Goniochromatic measurement method according to claim 1, wherein the particles are incorporated into a transparent medium comprising a nitrocellulose lacquer or nail varnish.

9. Goniochromatic measurement method according to claim 1, wherein the particles are pigments or fillers.

10. Goniochromatic measurement method according to claim 1, wherein the particles are fillers.

11. Goniochromatic measurement method according to claim 1, wherein the particles are selected from the group consisting of: synthetic organic polymers, polymethyl methacrylate, methyl methacrylate cross-polymer, natural mica, synthetic mica, natural or synthetic mica flakes coated with one or more metal oxides, coated or uncoated $SiO_2$ flakes, coated or uncoated $Al_2O_3$ flakes, nylon powder, pure or filled melamine resins, talc, $SiO_2$, glass powder, glass beads, coated or uncoated glass flakes, BiOCl, kaolin, oxides or hydroxides of aluminium, magnesium, calcium or zinc, barium sulfate, calcium sulfate, calcium carbonate, magnesium carbonate, basic alkaline-earth metal carbonates, carbon, boron nitride, zeolites, bentonites, alkali metal aluminium silicate beads coated with titanium dioxide and silicon dioxide, silicates of aluminium, magnesium, calcium, barium or zinc, or alkali metal silicates of aluminium, magnesium, calcium, barium or zinc.

12. Goniochromatic measurement method according to claim 1, wherein the illumination angle is 45° and the luminance is measured at the following angles along the semi-circle extending above the plane of the dark support:

| |
|---|
| 5° |
| 15° |
| 25° |
| 65° |
| 75° |
| 85° |
| 90° |
| 95° |
| 105° |
| 115° |
| 125° |
| 135° |
| 145° |
| 155° |
| 165° |
| 175°. |

13. A method for determination of the soft-focus factor (SFF=Lw/Lg) of fillers and pigments, where, in the CIEL*a*b* standard colour system, Lg is the L* value at the specular angle and Lw describes the luminance or whiteness of the filler/pigment L* at 65, comprising subjecting said fillers and pigments to a goniochromatic measurement method according to claim 1.

14. Goniochromatic measurement method according to claim 1, wherein the particles are incorporated into a transparent medium and the transparent medium is a coating.

15. Goniochromatic measurement method according to claim 1, wherein the particles are incorporated into a transparent medium and the transparent medium is a coating film.

16. Goniochromatic measurement method according to claim 15, wherein the transparent medium is dried and the dried coating film comprises 1-30% by weight of the particles.

* * * * *